(12) United States Patent
Hadzic et al.

(10) Patent No.: US 7,689,292 B2
(45) Date of Patent: Mar. 30, 2010

(54) NERVE STIMULATION FUNCTIONALITY INDICATOR APPARATUS AND METHOD

(75) Inventors: Admir Hadzic, Montclair, NJ (US); Alen Hadzic, Montclair, NJ (US); Nihad Hadzic, Wappingers Fall, NY (US); Giglioli Sergio, Mo (IT); Franca Gelatti, legal representative, Mirandola (IT); Jerry Vloka, Upper Saddle River, NJ (US); Howard Donnelly, Needman, MA (US)

(73) Assignee: Macosta Medical U.S.A., L.L.C., Houston, TX (US)

( * ) Notice: Subject to any disclaimer, the term of this patent is extended or adjusted under 35 U.S.C. 154(b) by 405 days.

(21) Appl. No.: 10/375,678

(22) Filed: Feb. 27, 2003

(65) Prior Publication Data

US 2004/0172114 A1 Sep. 2, 2004

(51) Int. Cl.
*A61N 1/00* (2006.01)
*A61B 5/05* (2006.01)
*A61B 18/18* (2006.01)

(52) U.S. Cl. .................. 607/150; 600/554; 606/44
(58) Field of Classification Search .......... 600/554, 600/373–374, 380, 546–548; 607/42–43, 607/45–49, 115–118, 150, 1–2; 606/32, 606/34, 36, 41, 44
See application file for complete search history.

(56) References Cited

U.S. PATENT DOCUMENTS

| 4,515,168 | A | * | 5/1985 | Chester et al. | ............... 600/554 |
|---|---|---|---|---|---|
| 5,092,344 | A | | 3/1992 | Lee | |
| 5,211,175 | A | | 5/1993 | Gleason et al. | |
| 5,284,154 | A | * | 2/1994 | Raymond et al. | ............ 600/554 |
| 5,775,331 | A | * | 7/1998 | Raymond et al. | ............ 600/554 |
| 6,259,945 | B1 | * | 7/2001 | Epstein et al. | ............... 600/547 |
| 6,325,764 | B1 | * | 12/2001 | Griffith et al. | ............... 600/554 |
| 6,706,016 | B2 | * | 3/2004 | Cory et al. | .................. 604/117 |
| 2002/0065481 | A1 | | 5/2002 | Cory et al. | |
| 2003/0167021 | A1 | * | 9/2003 | Shimm | ........................ 600/554 |

FOREIGN PATENT DOCUMENTS

DE       3719353 A1 * 12/1988

OTHER PUBLICATIONS

Supplementary European Search Report dated Dec. 2, 2009 from EP 04 70 5589.

* cited by examiner

*Primary Examiner*—Carl H Layno
*Assistant Examiner*—Jessica Sarcione
(74) *Attorney, Agent, or Firm*—Fitch Even Tabin & Flannery

(57) ABSTRACT

An operational status display for a nerve stimulator is located remote from the nerve stimulator. In one embodiment the display comprises a stand-alone discrete component that can be placed as desired by the nerve stimulator needle. In another embodiment, the display comprises an integral part of the nerve stimulator needle. The display can be alphanumeric or can comprise one or more discrete signal lights or other visual indicia. Color can be used to provide information regarding levels (intensity) of current, or the energy being provided to the needle and/or being delivered to the patient. In some embodiments these displays also provide information regarding the presence or absence of current and/or the polarity of the electricity then being provided to the nerve stimulator needle.

9 Claims, 3 Drawing Sheets

NERVE STIMULATION FUNCTIONALITY INDICATOR APPARATUS AND METHOD

TECHNICAL FIELD

This invention relates generally to nerve stimulation with electric current.

BACKGROUND

Anesthesiologists often use nerve stimulation to localize a desired nerve or nerves prior to administration of a local anesthetic (Von Perthes is generally credited with providing the original description of using peripheral nerve stimulators for regional anesthesia in 1912). Nerve stimulation typically utilizes electric current to elicit visible muscle twitches as a result of stimulation of the nerve or nerves to thereby confirm proximity of the needle to the nerve. This technique relies generally upon two phenomena. First, that many nerves, when properly stimulated by electric current, will cause a corresponding substantially predictable movement (such as a twitch) of a portion of the patient's body (in particular, muscle contractions resulting from stimulation of the nerve(s)). Second, that the amount of electric current required to cause the desired muscle movement will vary predictably with distance between the tip of the needle that sources the electric current and the nerve.

Stimulation typically begins with a higher intensity current (such as, for example, 1.5 to 2.0 milliamperes). Upon observing the anticipated muscle movement (thereby indicating that the needle is positioned within a given distance from the nerve, the current is reduced and the process repeated until the current has been reduced to a predetermined range (such as 0.2 to 0.5 milliamperes), thereby indicating that the needle is within a clinically relevant distance from the nerve to best facilitate the anesthesia of the nerve after introduction of a local anesthetic via the needle. When conducting this kind of procedure, it is important to avoid contacting or piercing the nerve with the needle as this can cause injury to the nerve. Generally, stimulation of the nerve with low current intensity (e.g., less than 0.5 milliamperes) indicates an intimate needle-nerve relationship and advancing the needle closer to the nerve after the stimulation is achieved at less than 0.5 milliamperes caries a risk of contacting or piercing the nerve.

The procedure typically requires two people. One person handles manipulation of the needle and observes the patient's response while the second person operates the remote peripheral nerve stimulator apparatus and visually monitors the current delivered. In particular, the latter person controls the amount of current being applied via the needle (as well as other parameters that pertain to the current being provided). For a variety of good reasons (e.g., lack of space, difficulty of placing the stimulator on the patient, preserving the sterile field, and so forth) the remote peripheral nerve stimulator itself is usually located at a certain distance away from the patient and the person manipulating the needle. The person manipulating the needle therefore must manage a consider degree of cognitive loading; they must physically manipulate the needle in a careful fashion while also observing the anticipated muscle response and also while remaining cognizant of the present amount of current being delivered via the needle. This person typically keeps verbally informing the person performing the block of the intensity of the current being delivered, so that the person performing the block does not have to frequently shift their gaze from the procedure to the display on the nerve stimulator and thus be distracted from the procedure. This can still require, in many instances, a considerable amount of frequent gaze shifting and/or repositioning by the person performing the procedure, particularly when the current gauge (or other indicator) on the nerve stimulator apparatus is located some distance away from the needle operator. Not surprisingly such physical and mental challenges give rise to a situation where errors are more likely to occur. These errors can be a direct result of the need for gaze alteration and distraction and typically include unwanted needle movement during gazing, which in turn may result in failure to anesthetize the nerve or piercing the nerve when the needle is inadvertently pushed deeper or pulled back more superficially from its original location. In addition, even when a single person performs the block and manipulates the stimulator at the same time (rare, but possible by use of a remote controller of the nerve stimulator, such as a foot pedal), the need to constantly shift one's gaze between the patient, needle, procedure, and the display on the nerve stimulator can still be very distracting.

The above approach is encumbered with other concerns and issues as well. For example, it is possible for the needle operator to insert the needle into the patient and to begin to manipulate it before the nerve stimulator apparatus operator has begun to provide current to the needle. It is also possible for the supply of electric current to fail during the procedure, such that the needle operator continues to manipulate the needle while unaware of this condition. Such conditions can result in discomfort and/or harm to the patient and/or an unsuccessful procedure. As another example, it is possible for the cord that couples the nerve stimulator apparatus to the needle to be improperly coupled to one or the other device or to become partially or fully disconnected during the procedure. This can result in either a complete failure to deliver current to the needle or a partial failure (where, for example, only a portion of the indicated current is actually being delivered to the needle). It is also possible for miscommunication to occur between the operator of the needle and the person operating the nerve stimulator, resulting in decisions made by the person operating the needle being inconsistent with the actual present electric current intensity.

Nerve stimulator devices typically have at least one indicator to represent the operational status of the machine. Light emitting diode meters, liquid crystal displays, flashing diodes, gauges of various types, and audible beeps, for example, have all been used to monitor current availability and/or to signal a malfunction. Such remotely placed indicia, unfortunately, doesn't always adequately serve the operator who manipulates the needle. Tight operating quarters and physical remoteness of the nerve stimulator machine can make it difficult for the needle operator to accurately view such visible displays, as can the required physical positioning and posturing of the needle operator during a given procedure. Furthermore, audible alerts are easily confused with other ordinary sounds of the operating theater (for example, patients receiving a nerve block are usually monitored by pulse oximetry which is also typically accompanied by an audible beeping sound).

BRIEF DESCRIPTION OF THE DRAWINGS

The above needs are at least partially met through provision of the nerve stimulation functionality indicator apparatus and method as described in the following detailed description, particularly when studied in conjunction with the drawings, wherein.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are typically not depicted in order to facilitate a less obstructed view of these various embodiments of the present invention.

DETAILED DESCRIPTION

Generally speaking, pursuant these various embodiments, a nerve stimulator operational status display is disposable in an operational mode substantially distal to the nerve stimulator (thereby permitting its placement in a more convenient location for the person manipulating the needle). This display couples to the nerve stimulator via an appropriate nerve stimulator operational status information communication path. In some embodiments, the display is separate (or separable) from both the nerve stimulator and the nerve stimulator needle. In a preferred embodiment, such a separate display includes an attachment mechanism such that the nerve stimulator operational status display can be temporarily attached to an object that is distal to the nerve stimulator (such as, for example, the needle operator or the patient's garb). In other embodiments, such a display is provided integral to the needle (such as, for example, by comprising a part of a hand graspable hub of the needle).

In various embodiments, the nerve stimulator operational status information communication path can comprise any of an electrical conductor, an optical conduit, and/or a wireless channel.

The display can present signal indicia and/or alphanumeric information regarding current as being delivered to the needle. Depending upon the embodiment, the display can also provide information regarding current presence and/or polarity of the current being provided. In some embodiments, color serves to indicate the amount of current being provided to the needle.

So configured, the needle operator can readily remain apprised of various data regarding the provision of current to the needle without needing to significantly alter his or her posture, position, or general field of view. Furthermore, the needle operator can receive accurate and timely information regarding the present availability of current and the polarity of the corresponding voltage potential, thereby avoiding inappropriate manipulation of the needle when current becomes unavailable or unsuitable for whatever reason.

Figure 1:
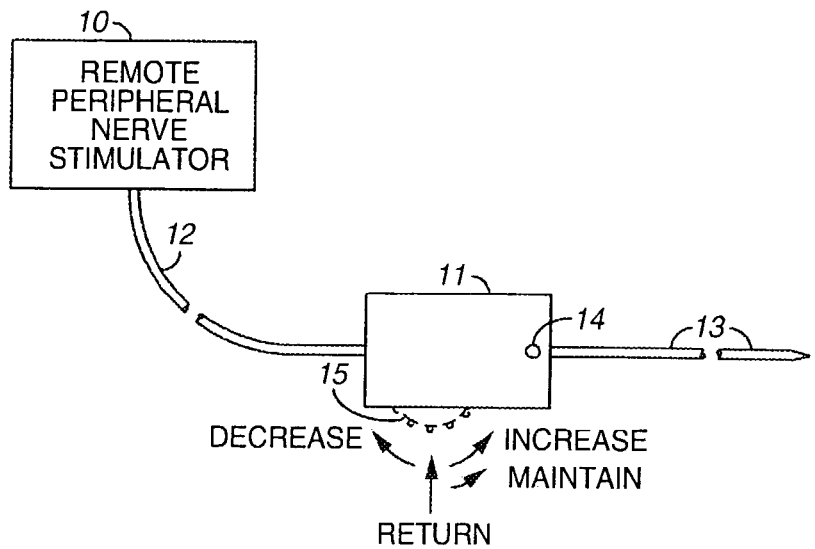
FIG. 1 comprises a system block diagram as configured in accordance with various embodiments of the invention.

Referring now to the drawings, and in particular to FIG. 1, a remote peripheral nerve stimulator as is generally known in the art couples via an electrical tether 12 to a nerve stimulation needle comprised of a hand graspable hub 11 and a needle 13. In this embodiment, the electrical tether 12 couples to and extends outwardly of the hand graspable hub 11. In this embodiment, the hand graspable hub 11 also includes needle functionality indicia 14 comprising non-alphanumeric visible indicia. As depicted, in this embodiment, the visible indicia comprises a discrete representational indicia such as, for example, a light emitting diode. In a preferred embodiment, the light emitting diode would comprise a multi-color light emitting diode (or a multitude of various colored diodes) such that different displayed colors can be used to represent different corresponding amounts of current then being provided to the needle as described in more detail herein. In addition, such a discrete indicia can also serve to present information regarding a presence or absence of electrical current and/or the polarity of electricity then being provided to the needle.

Figure 2:
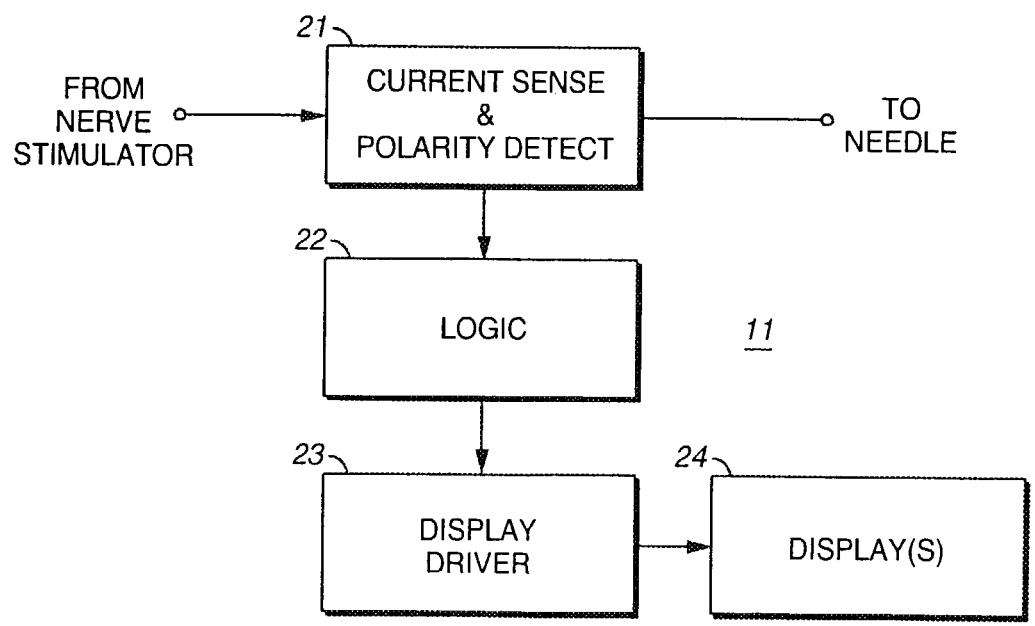
FIG. 2 comprises a block diagram of a needle hub as configured in accordance with an embodiment of the invention.

With reference now to FIG. 2, the nerve stimulator needle 11 can include a current sense unit 21 (with polarity detection capability too, if desired) to detect the presence and amount of current being provided by the nerve stimulator to the needle. Any number of known current detection circuits can be utilized to enable this capability. The current sense unit 21 provides its locally developed information to a logic unit 22 where a determination can be made regarding the presence and amount of current then being provided to the needle and for then correlating that determination to a particular corresponding visual indication. The logic unit 22 can be a programmable platform, a hard-wired logic circuit, or a combination of both as well understood in the art. The logic unit 22 then provides the information via a coupling circuit (such coupling circuits being well known in the art) to display information to a display driver 23 which then causes the information to be displayed by the display 24 (or displays where more than one display is provided). For example, when the display 24 comprises a multicolor light emitting diode as disclosed above, the logic unit 22 can identify the specific color that will serve to represent the detected current level and the display driver 23 can translate that selection into specific trigger signals that cause the light emitting diode to glow with that particular color.

Figure 3:
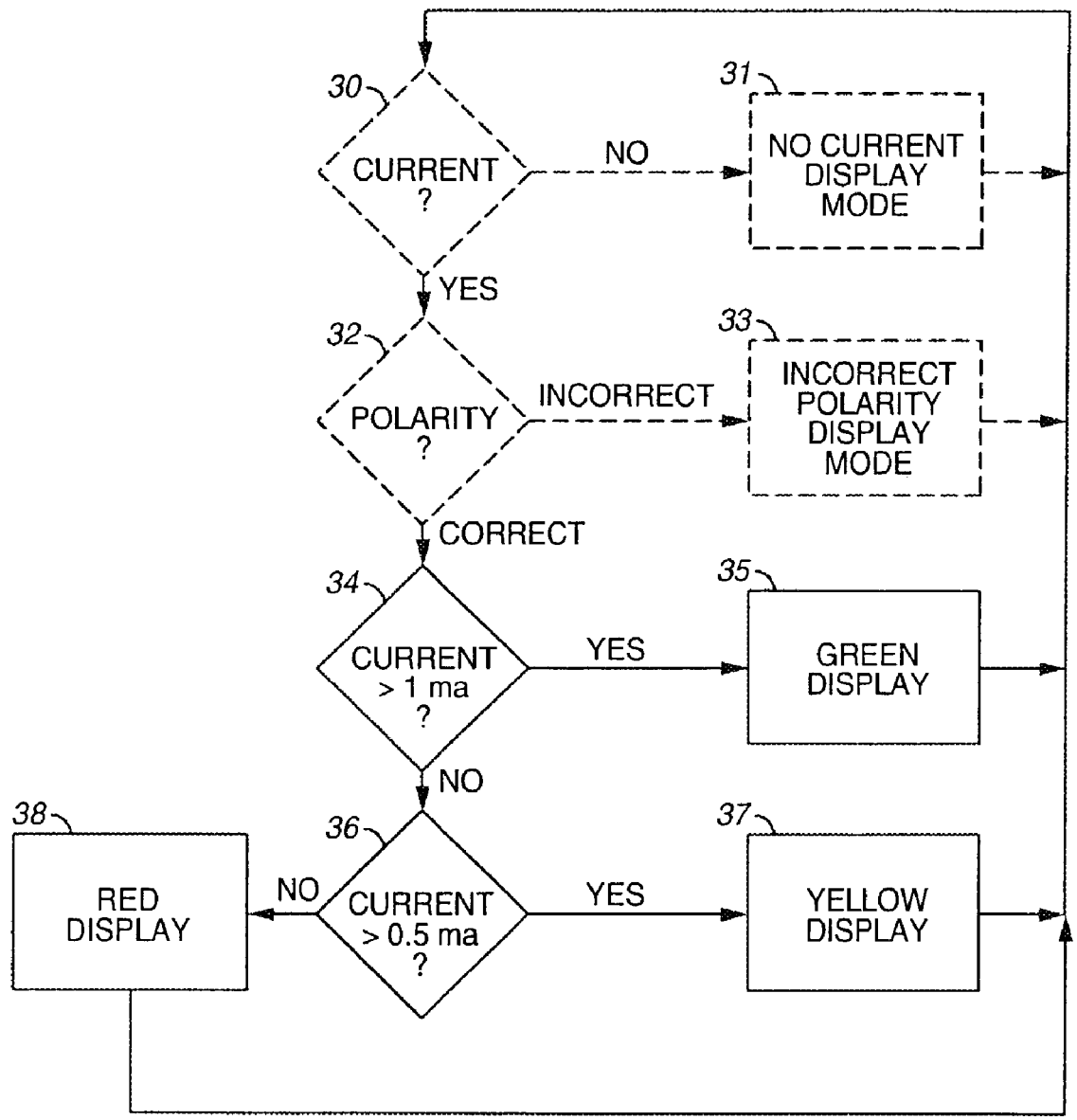
FIG. 3 comprises a flow diagram as configured in accordance with an embodiment of the invention.

FIG. 3 serves to illustrate one approach to such an embodiment. The logic unit 22 can optionally test 30 for the presence of current as described above. Upon determining that no current is presently being provided, the logic unit 22 can effect a display 31 that corresponds to such a determination (for example, by extinguishing the light emitting diode). When current is present, the logic unit 22 can also optionally test 32 the polarity of the connection between the nerve stimulator 10 and the nerve stimulator needle. When incorrect polarity is evident, the logic unit 22 can effect an appropriate corresponding display 33. When current is present and the electric connection has appropriate polarity, the logic unit 22 then determines the amount of current that is present. In this illustrative embodiment, when more than 1.0 milliamperes is present 34, a green display is provided 35 through appropriate control of the multi-color light emitting diode. When less than 1.0 milliamperes but more than 0.5 milliamperes is detected 36, a yellow display 37 can be provided. And, when less than 0.5 milliamperes is detected 36, a red colored display can be provided 38.

So configured, the needle operator can readily determine what level of current is presently being utilized without needing to find and observe the nerve stimulator 10 itself. Instead, the display 14 on the hub 11 can be readily viewed to obtain such information.

Also, optionally, the needle operator can become similarly apprised of the general presence or absence of current and/or the polarity of the electricity being delivered to the nerve stimulator needle, again without needing to substantially break attention and focus with respect to manipulation of the needle itself.

Figure 4:
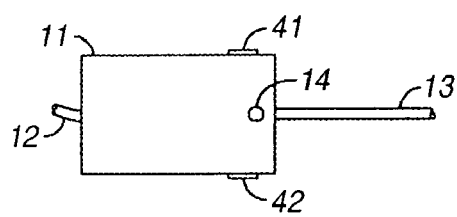
FIG. 4 comprises a detail block diagram as configured in accordance with an embodiment of the invention.
Figure 5:
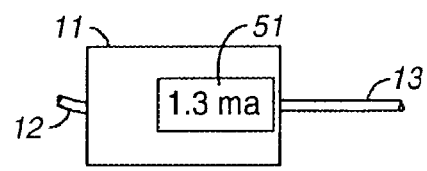
FIG. 5 comprises a detail block diagram as configured in accordance with another embodiment of the invention.

In the illustrative examples above, only a single visual point source serves to provide the desired information. Other configurations are of course possible. For example, with reference to FIG. 4, additional selectably illuminable indicia 41 and 42 can be additionally disposed on the hub 11. Such additional indicia can serve to better accommodate a wider range of useful viewing angles such that the needle operator can be assured a useful view of a display from many different working perspectives almost regardless of the needle operator's position with respect to the hub 11. As another example, and referring now to FIG. 5, other kinds of displays can also be used including, for example, an alphanumeric or other graphic element display 51. Such a display 51 can be embodied by a liquid crystal display or any other functionally similar display that meets the needs and requirements of a given implementation. Such a display can serve to directly display a specific amount of current as is then being provided to the needle. In addition (or in lieu thereof, such a display can use color as otherwise suggested above to provide information regarding the present operational status of the needle's current.

Figure 6:
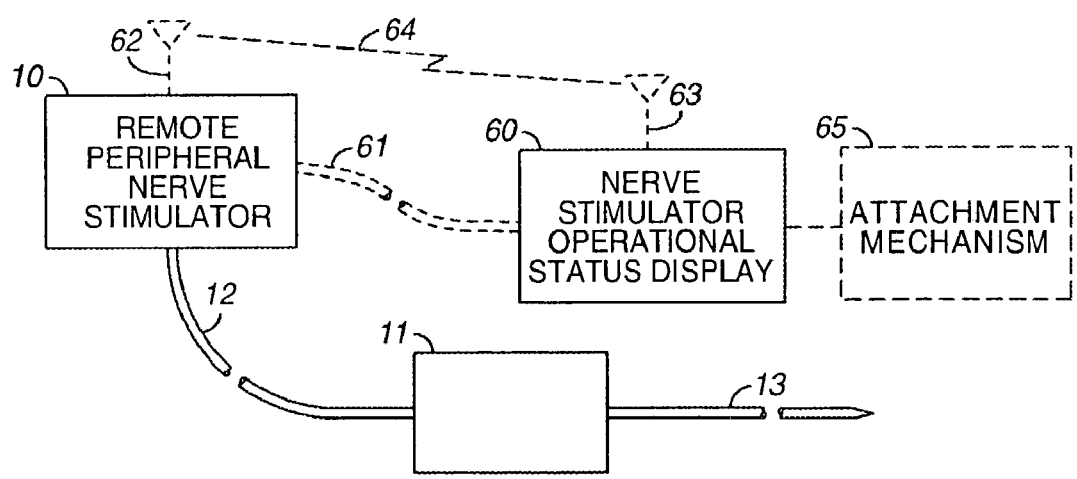
FIG. 6 comprises a system block diagram as configured in accordance with yet another embodiment of the invention.

In the various embodiments described above, the display comprises an integral part of the nerve stimulator needle. In other embodiments, however, the display may be separate from the nerve stimulator needle and also remote from the nerve stimulator 10. For example, and referring now to FIG. 6, a separate and discrete nerve stimulator operational status display 60 (preferably as provided with its own discrete housing) can couple to the nerve stimulator independent of the needle via a dedicated nerve stimulator operational status information communication path 61. This path can comprise, as desired, an electrical conductor, an optical fiber, and/or a wireless communications channel 64 (including any of radio frequency-based signaling such as a Bluetooth-compatible channel, infrared-based signaling, and so forth) when both the nerve stimulator 10 and the display 60 are appropriately equipped with the necessary transmission and reception capability (represented here by the optional inclusion of antenna as denoted by reference numerals 62 and 63).

So configured, during operational use, the display 60 can be disposed remote from the nerve stimulator 10 and proximal to a desired viewing location as determined, for example, by the needle operator. If desired, to facilitate such placement, the display 60 can be further equipped with an attachment mechanism 65 (such as Velcro-style hooks or loops, pins, snaps, clips, or any other attachment mechanism as may be presently known or hereafter developed). The display 60, of course, can be otherwise configured as described and suggested above to thereby provide all of the same benefits and advantages in a potentially more convenient-to-view embodiment.

Again, it can be seen that all of these embodiments serve generally to permit a needle operator to effect the nerve stimulation process with greater certainty and less physical and mental challenge than was previously possible under most normal circumstances. In general this should result in more rapid completion of the process and a reduction in overall discomfort for the patient.

Such embodiments not only improve the convenience by which a needle operator can obtain information regarding the operational status of the nerve stimulation process, they can also be used to facilitate a positive alteration of the nerve stimulation process itself. For example, instead of functioning as potentially both a receiver of information from and a provider of instructions to the nerve stimulator operator, the needle operator can more intuitively rely upon the displayed information to remain apprised of current operating conditions such that the dialogue between the two operators can comprise more unambiguously a series of instructions from the needle operator to the nerve stimulator operator.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

For example, the embodiments presented describe a display mechanism that is driven by an active logic capability that is remote from the nerve stimulator 10. If desired, of course, such logic capability could be disposed within the nerve stimulator 10 and the extracted information then communicated to the display. This could be accomplished via an active reception and decoding capability or more passively if desired (for example, a fiber optic cable could be used to transmit indicia light from the nerve stimulator 10 to a viewing point on the nerve stimulator needle or on the discrete and separate display housing to essentially permit remote viewing of an indicator light that is located back with the nerve stimulator 10).

As another example, flashing one or more portions of a given display can be used to indicate either correct operation or incorrect operation. For example, a flashing light emitting diode could be used to indicate the presence of current (or the absence thereof) and an extinguished diode could be used to indicate the opposite condition.

And as yet another example, a user input mechanism (such as a multi-position switch 15 as is shown depicted in phantom lines in FIG. 1 to denote its optional status) can be provided on the needle (and, in a preferred approach, on the hub 11). Such a mechanism could be used by the person manipulating the needle to provide information, such as instructions regarding the provision of electric current, to the nerve stimulator operator. Such instructions could indicate, for example, that the nerve stimulator operator should increase the electrical current, decrease the electrical current, or maintain the electrical current at a particular level (for example, a multi-position switch 15, such as a wheel switch that is biased to return to a return point, could be rotated in one direction to indicate that current should be decreased, rotated slightly in the opposite direction to indicate that the current should be maintained at a present level, and rotated fully in the opposite direction to indicate that the current should be increased). So configured, the needle operator would have an additional option of communicating specific instructions to the nerve stimulator operator via this mechanism. Such a capability could be useful in a variety of circumstances, and particularly so when the immediate vicinity of the patient becomes sufficiently noisy that verbal communications between the needle operator and the nerve stimulator operator are rendered more difficult.

We claim:

1. A nerve stimulator needle for use with a nerve stimulator that provides electric current in response to settings set by a nerve stimulator operator for use by the nerve stimulator needle to elicit visible muscle twitches in a patient and where the nerve stimulator is located remotely from the nerve stimulator needle, the nerve stimulator needle lacking any user interface to directly control the electric current being provided by the nerve stimulator and otherwise comprising:

a needle;

a hand-graspable hub from which the needle extends;

an electrical tether extending from the hand-graspable hub and being configured to connect to the nerve stimulator to thereby convey the electric current from the nerve stimulator to the needle;

a current sense unit disposed within the hand-graspable hub and being configured to detect a presence and amount of electric current being conveyed from the nerve stimulator to the needle;

a display driver disposed within the hand-graspable hub and operably coupled to the current sense unit; and a display disposed on the hand-graspable hub and being operably coupled to the display driver, the display being configured to present information regarding the presence and amount of electric current being conveyed from the nerve stimulator to the needle; such that a needle operator who is manipulating the needle via the hand-graspable hub and who is different from the nerve stimulator operator remains informed during a nerve stimulation procedure regarding the presence and amount of electric current then being delivered by the needle to the patient by referring to the display and without looking towards the nerve stimulator itself.

2. The nerve stimulator needle of claim 1 wherein the display comprises a multicolor display.

3. The nerve stimulator needle of claim 1 wherein the display comprises a graphic display.

4. The nerve stimulator needle of claim 3 wherein the graphic display comprises an alphanumeric display.

5. The nerve stimulator needle of claim 1 wherein the display is further configured to display information regarding a polarity of the electric current.

6. The nerve stimulator needle of claim 1 further comprising:

a user-input mechanism on the hand-graspable hub that is configured to permit the needle operator to convey instructions to the nerve stimulator operator.

7. The nerve stimulator needle of claim 6 wherein the user-input mechanism is configured to permit the needle operator to convey instructions to the nerve stimulator operator regarding provision of the electric current.

8. The nerve stimulator needle of claim 7 wherein the instructions convey that the electric current is to be increased by the nerve stimulator operator.

9. The nerve stimulator needle of claim 7 wherein the instructions convey that the electric current is to be decreased by the nerve stimulator operator.

* * * * *